(12) United States Patent
Nitz

(10) Patent No.: US 7,280,992 B2
(45) Date of Patent: Oct. 9, 2007

(54) METHOD FOR PROCESSING MEDICALLY RELEVANT DATA

(75) Inventor: Wolfgang Nitz, Buch (DE)

(73) Assignee: Siemens Aktiengesellschaft, Munich (DE)

( * ) Notice: Subject to any disclaimer, the term of this patent is extended or adjusted under 35 U.S.C. 154(b) by 759 days.

(21) Appl. No.: 10/292,658

(22) Filed: Nov. 12, 2002

(65) Prior Publication Data

US 2003/0092980 A1    May 15, 2003

(30) Foreign Application Priority Data

Nov. 15, 2001 (DE) .................... 101 56 215

(51) Int. Cl.
*G06F 17/00* (2006.01)
(52) U.S. Cl. .................... 706/46; 600/300; 705/2; 382/128
(58) Field of Classification Search ............... 600/407, 600/300; 706/45; 382/128; 705/2
See application file for complete search history.

(56) References Cited

U.S. PATENT DOCUMENTS

| 5,517,405 A | 5/1996 | McAndrew et al. |
| 5,572,422 A * | 11/1996 | Nematbakhsh et al. ........ 705/3 |
| 6,247,004 B1 * | 6/2001 | Moukheibir ............... 600/300 |
| 6,648,820 B1 * | 11/2003 | Sarel ........................ 600/300 |

FOREIGN PATENT DOCUMENTS

| DE | 198 09 952 | 9/1999 |
| EP | 0 741 361 | 11/2001 |

* cited by examiner

*Primary Examiner*—Brian L. Casler
*Assistant Examiner*—John F. Ramirez
(74) *Attorney, Agent, or Firm*—Schiff Hardin LLP

(57) ABSTRACT

In a method and system for processing medically relevant data in the framework of an examination of a patient that is to be implemented, a program is installed in a data processing device that selects one or more examination modalities to be implemented for the examination of the patient on the basis of symptom-specific and/or diagnosis-specific information that have been entered and using symptom-based and/or diagnosis-based data bank. The examination modalities are available as an output at a playback device.

28 Claims, 3 Drawing Sheets

METHOD FOR PROCESSING MEDICALLY RELEVANT DATA

BACKGROUND OF THE INVENTION

1. Field of the Invention

The present invention is directed to a method for processing medically relevant data in the framework of an examination of a patient that is to be implemented.

2. Description of the Prior Art

The decision about examination modalities, i.e. the examination facilities (for example, X-ray examination, computed tomography, magnetic resonance), and about the examination or measurement protocol with which a patient is to be examined in the framework of a diagnostic examination, particularly in the framework of radiology, is a process of increasing complexity with a great number of communication locations at which information can be lost. A first anamnesis is made by the family physician, the general practitioner, who, given a more complicated clinical picture that makes further diagnosis by a specialist necessary, prepares a "tentative diagnosis" for referral to a specialized colleague, for example a specialist in internal medicine, a cardiologist or radiologist. Within the framework of a second anamnesis, the specialist reviews whether the examination modality suggested by the general practitioner is meaningful, i.e., for example, a magnetic resonance examination. The specialist is likewise under great pressure to remain current in view of the constantly increasing quantity of information relating to his/her specialty, for example current examination or measurement protocols, new examination and image acquisition methods, etc. Textbooks or technical periodicals are often consulted in the evaluation of the images that are registered with the imaging modalities, particularly given rare conditions.

It is thus not simple for the specialist, either, to determine the correct examination modality, or the correct examination modalities, and the appropriate sequence on the basis of the given anamnesis data, which include symptom-specific information of the patient as well as information from the referring physician, particularly his/her tentative diagnosis. In any case, the specializing is limited to his/her own state of knowledge in the framework of this determination, which in turn, is limited in view of the total amount of medical information. The above applies equally to the interpretation of the examination results that are obtained with the examination modality or the different examination modalities, particularly in the form of images. This, too, is highly dependent on the current state of knowledge of the attending physician. A certain degree of uncertainty always exists.

U.S. Pat. No. 5,517,405 discloses an expert system for the interactive support of a physician that serves the purpose of reviewing the correctness of a proposed treatment on the part of the physician for treating a condition of the patient that the physician diagnosed. To this end, the physician enters information relating to the patient as well as the patient's state of health, or a diagnosis of a disease as well as a proposed treatment for the disease, via an input medium. The treatment proposal entered by the physician is then reviewed for correctness on the basis of expert knowledge stored in a data bank, taking the state of health or clinical data of the patient into consideration.

Further, German OS 198 09 952 discloses a method for the configuration of monitors allocated to medical-technical devices that enables an individually desired presentation and display given changing operating personnel. European Application 0 741 361 discloses a system for the playback of a medical image with configurable text region represented by a digital signal presentation.

SUMMARY OF THE INVENTION

An object of the present invention is to provide a method and system that supports the physician in the framework of processing medically relevant data.

This object is inventively achieved in a method of the type initially described wherein a program deposited in a data processing device selects one or more examination modalities to be implemented for the examination of the patient on the basis of symptom-specific and/or diagnosis-specific information that has been entered and with use of a symptom-based and/or diagnosis-based data bank, the examination modalities being made available as an output at a playback device.

The inventive method especially advantageously makes use of a symptom-based and/or diagnosis-based data bank in which existing expert knowledge is compiled and is available to the physician. Those examination modalities that seem most expedient in view of the symptoms or the tentative diagnosis are selected from this data bank via a suitable program means to which symptom-specific and/or diagnosis-specific information relating to the patient have been entered. This selection ensues based on the entire, existing expert knowledge that can be consulted from the data bank by means of the program. The selection result thus is based on an immense quantity of data and an expert knowledge accumulated over years that the attending physician does not have available, no matter how well he/she has stayed current. As a result, an improved and—for the physician—significantly simplified determination of the most expedient examination modalities to be implemented is possible based on the existing symptom-specific and/or diagnosis-specific information. The selection of an incorrect or inexpedient examination modality that leads to an unnecessary stress on the patient (for example, radiation stress) and that involves an unnecessary loss of time, particularly in the case of a critical illness of the patient, as well as, an unnecessary expense, is thereby precluded to a far-reaching extent.

Expediently, the data bank itself is continuously updated with expert knowledge. This can ensue via a suitable expert commission that collects, sifts and evaluates relevant new perceptions and adds them to the data bank as needed. The certainty of the selection over time can be improved even further in this way on the basis of the constantly augmented information within the data bank on which the selection is based.

It is expedient when, given a selection of multiple modalities, the sequence of their implementation is indicated. The attending physician thus effectively receives a flowchart of the various examinations to be implemented, as seems most expedient based on the entire expert knowledge in view of the symptoms acquired in the framework of the anamnesis, or on the basis of the "tentative diagnosis" that is already known.

In a further embodiment, after the entry of the symptom-specific and/or the diagnosis-specific information, the informational content thereof is reviewed by the program or via the databank, and one or more questions to be put to the patient are subsequently selected from the data bank and presented as an output, the patient being asked these questions by the physician to whom the patient was referred, for example, by the general practitioner. The reply information is entered, and the reply information is likewise taken into consideration in the framework of the following selection of the examination modalities to be applied in the specific case. This is expedient in the event that, for example, the referring general practitioner has already implemented an initial anamnesis but this anamneses did not raise some important question or other, the relevance of which only becomes apparent from the totality of the existing expert knowledge. The data bank wherein the entire expert knowledge is present, however, is capable of filling any such "anamnesis gaps".

Another problem that exists for medical specialists is the determination of the examination or measurement protocol or protocols, i.e. the actual examination sequences and examination events that are implemented with an examination modality. These examination and measurement protocols ultimately define which region is examined and registered in the framework of the imaging examination, in which way and with which presentation. These protocols contain all relevant operating parameters that are required for the operation of the examination modality for the registration of the desired image. It is obvious that the quality of the examination and of the ultimate diagnosis is highly dependent on the selection of the correct examination or measurement protocol. It is also obvious that, for example using a magnetic resonance apparatus, a number of highly different examination or measurement protocols can be implemented, or corresponding examinations can be undertaken, so that the attending physician also experiences extreme demands to select the correct protocol or protocols. In order to also assist the attending physician in this, in an embodiment of the invention the data bank selects and outputs one or more examination or measurement protocols defining the examination for a specific examination modality. Since the data bank is also supported by expert knowledge in this selection (the expert knowledge, of course, also includes the examination or measurement protocols that can be implemented with a specific system), this selection also ensues on the basis of the current state of knowledge. The selection of the protocols ensues such that images that in fact show the relevant examination region and supply a basis for a diagnosis can be registered therewith. The protocols, of course, also contain corresponding information regarding resolution of the images to be acquired in order to be able to prepare a rational diagnosis on the basis of the exposures.

Of course, another important point in the framework of the image acquisition is that the images in fact show the plane of the organ under examination that is relevant for the diagnosis and that the images show the organ in a diagnostically relevant position. In a magnetic resonance apparatus, for example, the position of the image plane is usually set by the medical-technical radiology assistant. To avoid errors that would lead to images that have no or only little diagnostic relevance, it is expedient to make use of the expert knowledge data bank to select and output optical and/or acoustic information relating to the positioning of the image plane, when an imaging examination modality has been output. This information is presented in the framework of the examination or measurement protocols indicated therefor for the implementation of the examination by means of the examination modality. The radiology assistant thus is provided with information about where he/she must define the image plane in order to be able to acquire an image having optimum diagnostic relevance—proceeding on the basis of the expert knowledge underlying the general selection as well as the existing symptom-specific and diagnosis-specific information.

A positioning image that reproduces the examination region and into which the position of the image plane is mixed with one or more markings can be output as the aforementioned optical positioning information. For example, this positioning image shows an image of an arbitrary "comparison patient" that shows the examination region that is also to be examined in the patient being treated. For example, the position of the image plane is entered therein via a line. In this case, thus, the radiology assistant is presented with an exemplary image relating to the plane positioning. Alternatively, of course, this can also be output in the form of a text that, for example, is mixed in at a monitor or the like.

The positioning image together with a previously registered image of the patient can be output at a monitor, preferably in common, so that the radiology assistant can in turn check the selected position of the image plane. Instead of a position image, of course, there is also the possibility of playing a video that reproduces the relevant information.

In a further embodiment of the invention, after the implementation of an examination modality, symptom-specific and/or diagnosis-specific information determined therewith are entered, with one or more further examination modalities and/or examination or measurement protocols being selected and output as warranted based thereon. The totality of information thus is continuously expanded by newly acquired information that results from an implemented examination. The attending physician can confirm that a specific finding is present or is not present, as recognized from the evaluation of an initially implemented X-ray examination, for example. The system takes this information into consideration, and weighs and processes the information and, insofar as necessary, selects a further examination modality or a corresponding protocol, insofar as this is necessary and expedient based on the present state of the information and the general state of knowledge.

In the framework of processing the data, it is also expedient to select and output additional examination-relevant and/or diagnosis-relevant information for a proposed examination modality from the data bank via the program. This information, for example, can be guidelines of a relevant professional authority, such as the German Federal Physicians' Board, or earlier case examples, or current published references, or, in general, any and all additional information that can be of assistance to the physician in the framework of the pending examination.

In a further embodiment of the invention, following the exposure or one or more examination images of the examination region, possibly acquired with different examination modalities, one or more comparison images of a comparison examination region are output, and a patient image is presented at a monitor in common with a comparison image obtained from the data bank. This embodiment of the invention thus offers the attending physician a possibility for comparison by being shown a comparison image of, the same examination region that is stored in the data bank and that was registered for an arbitrary person once at an earlier time. In this way, the attending physician can unproblematically compare the patient image to the comparison image, which is very helpful for the diagnosis. The comparison image can be an image that shows the healthy examination region or one that shows the pathological examination region. The physician thus immediately recognizes what the pathological or non-pathological examination region looks like, so that he/she can analyze the patient image in view thereof and find differences. Of course, it is also possible in this context to use a number of examination images, for example in the form of a video recording, instead of a single examination image.

In a further embodiment, dependent on a diagnosis-specific information that is entered (diagnostic-specific information registered in the framework of the initial anamnesis or diagnosis-specific information obtained in the framework of the implemented examinations) the program in conjunction with the data bank selects and displays information that more specifically describe the condition diagnosed with the diagnosis-specific information. For example, following the implementation of a first X-ray examination, the physician may suspect a specific illness and enter this diagnosis-specific information, then corresponding information describing this illness in greater detail is selected from the data bank of the system side, this information containing, for example, a listing of the symptoms typical of the condition, the general course of the disease, etc. On the basis thereof, the physician can then orient himself/herself even better in the framework of interpretations of subsequently registered images.

In a further embodiment of the invention, the data processing device transmits input and/or selected information and/or examination or measurement protocols and/or comparison images and/or information describing the disease to a data processing device and/or control device of a selected examination modality that is employed for examining the patient. The transmittal information can be played back at the modality and/or directly employed for the control of the examination modality as needed. Insofar as required, the relevant data—no matter of what type—are transmitted to the data processing device and/or control device of the examination modality, so that the data are present at the respective examination modality at which the examination of the patient is to be subsequently implemented. The relevant information can be displayed for the attending physician or the radiology assistant directly at the monitor of, for example, a magnetic resonance apparatus and he/she can work on site with the relevant information.

The above object of the invention also is achieved in a system for processing medically relevant data in the framework of an examination of a patient that is to be implemented, having a data processing device with an installed program means and a playback device, the system being fashioned for the implementation of the described inventive method.

The system is further characterized by the data processing device having a communication links to a data processing device and/or control device of one or more medical examination modalities for the transmission of data in order to enable the above-described data transfer.

The system is further characterized by the data bank being in communication with an image archiving and patient information system for communication of the stored anamnesis, the communication of the image information of a "normal" comparison anatomy, the communication of the image information that correspond to the "tentative diagnosis", the communication of quantitative "normal values", and the communication of "standardized" findings texts.

In the inventive system, the data bank can be in communication with the attending physician location for the communication of the stored anamnesis as a "tentative diagnosis", and the system can propose pre-formulated findings texts to the diagnosing physician corresponding to the diagnosis to be confirmed or for the exclusion of pathological modifications.

DESCRIPTION OF THE PREFERRED EMBODIMENTS

Figure 2:
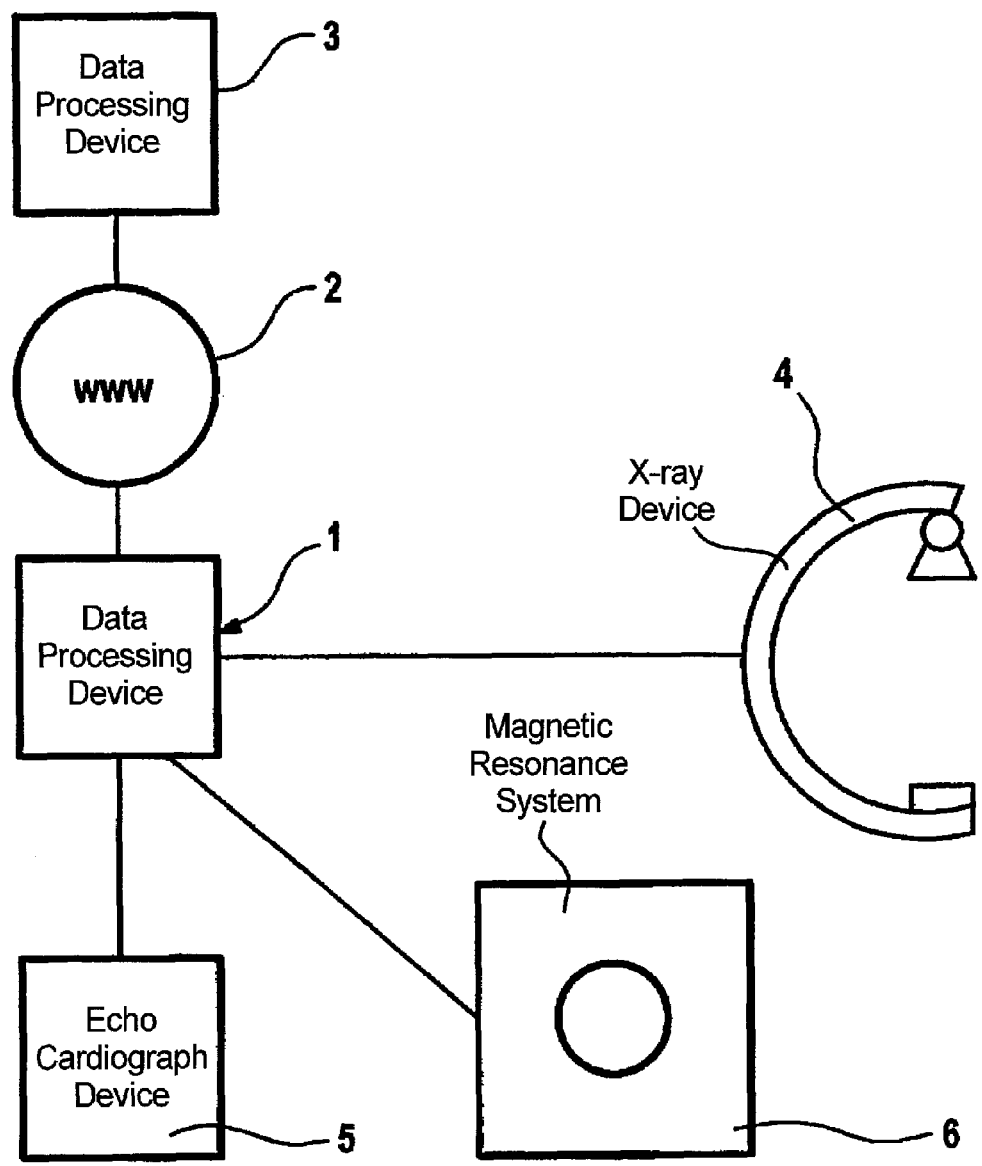
FIG. 2 is a schematic diagram of an inventive system suitable for the implementation of the method.

The inventive system according to FIG. 2 shall be described first. The system has a data processing device 1 into which a program (which can be a combination of multiple sub-programs) having a symptom-based or diagnosis-based data bank can be downloaded on demand from an external data processing device 3 via the Internet 2 in the illustrated exemplary embodiment. First, this program can be continuously accessed and downloaded; second, corresponding updates are also available via this route. The maintenance of the program or of the data bank ensues, for example, via a central board of a number of experts who continuously collect the newest perceptions, exemplary cases, etc., review them for their content and relevance, and incorporate them as warranted into the data bank.

The program ultimately deposited in the data processing device 1 is fashioned for the implementation of the method described below. As FIG. 2 also shows, the data processing device 1 has a communication link to various examination modalities. One examination modality is, for example, an X-ray apparatus 4, a second is an echocardiography apparatus 5 and a third is a magnetic resonance apparatus 6. The data processing device 1 forwards suitable data—as discussed below—that also can include control information to the respective examination modality to be placed in operation, the latter then presenting this data at suitable monitors, or directly acting on the data in the control portion of the modality.

Figure 1A:
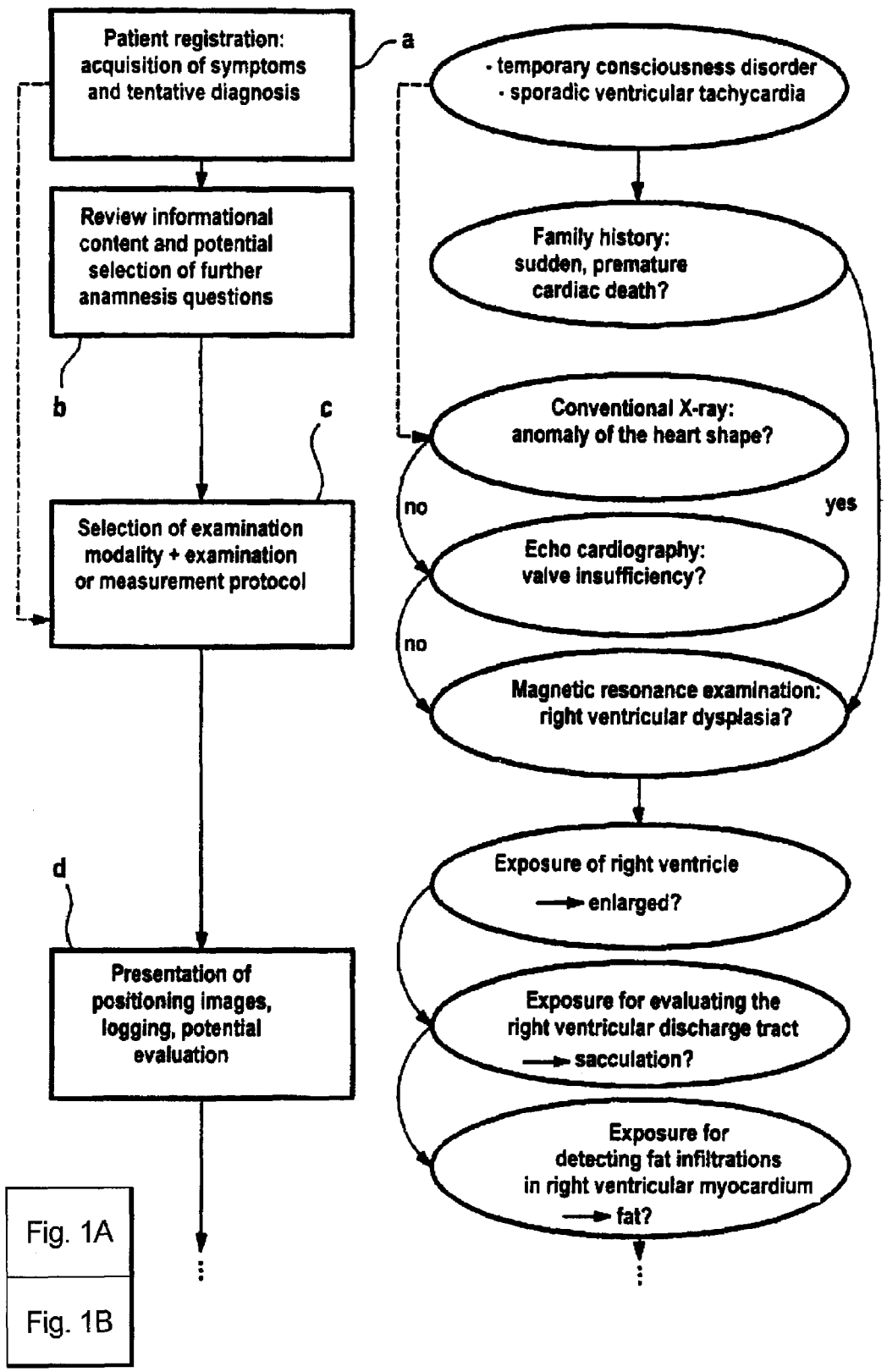
FIGS. 1A and 1B form a flowchart for schematically presenting of the executive sequence of the inventive method.
Figure 1B:
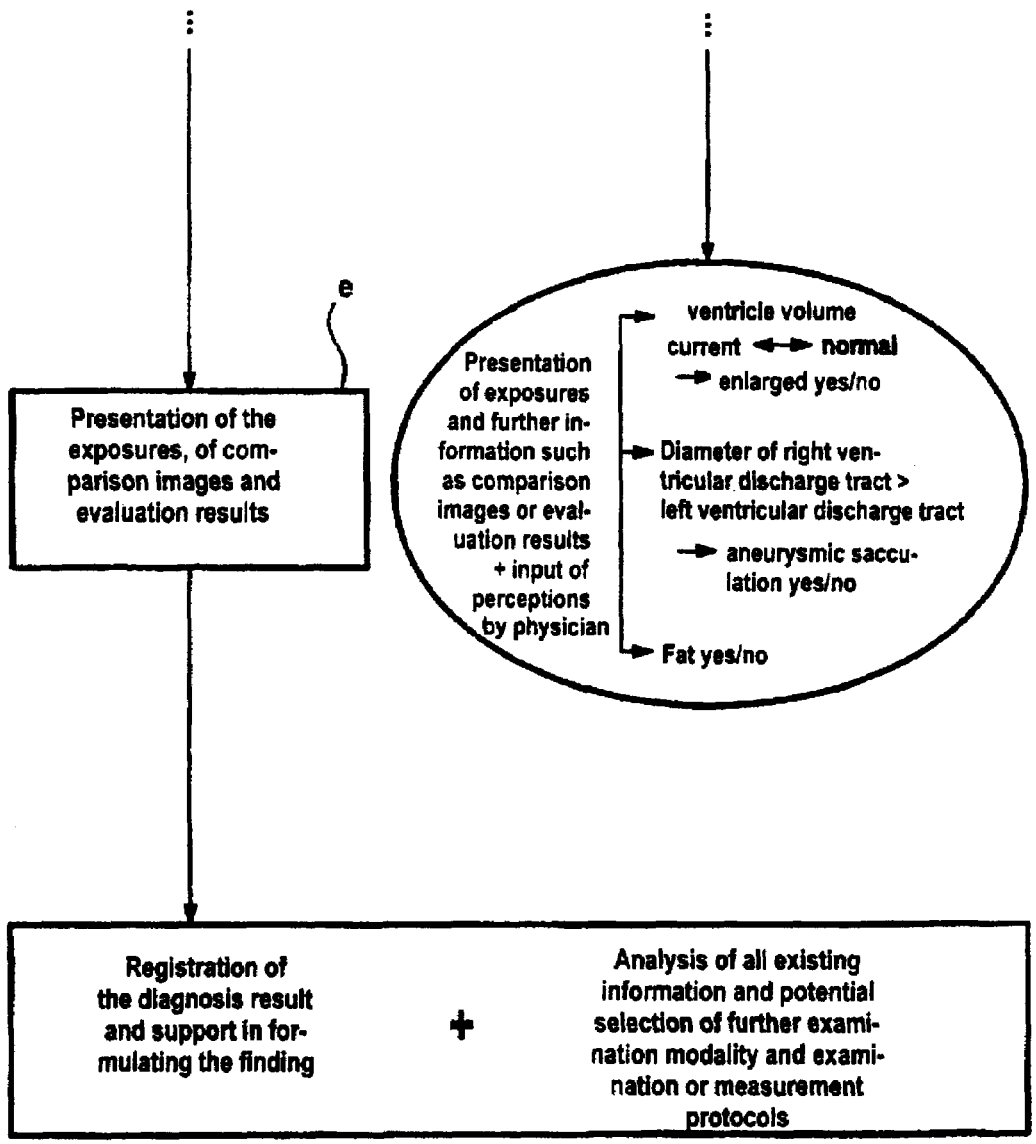

In the form of a schematic flowchart, FIGS. 1A and 1B show the operation of the inventive method. FIG. 1A follows FIG. 1B (as indicated in each of FIGS. 1A and 1B).

A patient consults a general practitioner who finds in the framework of an anamnesis in step (a) that the patient is complaining about sporadic ventricular tachycardia and that brief-duration losses of consciousness occur that, for example, caused the patient to have a traffic accident. The general practitioner suspects a heart condition, for which reason he/she refers the patient to a specialist, a radiologist in this case.

At the radiologist's practice, for example in a clinic, the patient registration initially ensues according to step (a). In the framework of this registration, among other things, the symptoms already detected by the general practitioner in step (a), i.e. symptom-specific information, as well as a tentative diagnosis made by the general practitioner, i.e. diagnosis-specific information, are entered into the data processing device in which the program is already present. These, subsequently, are the symptoms "temporary consciousness disorder" and "sporadic ventricular tachycardia". It should be noted that the method steps that ensue on the part of the program or on the basis of the program are respectively recited in the rectangular boxes at the left in the FIGS. 1A and 1B, whereas the examination-relevant steps are respectively shown in the rounded boxes at the right.

In step (b), the program reviews the content of the entered information for relevance and may select one or more further anamnesis questions that are relevant for the further method execution. As described, the program includes a data bank in which optimally extensive expert knowledge is deposited. The described information interpretation and review as well as the possible selection of questions ensue on the basis of this knowledge. In the illustrated example, a question about the family history is additionally asked, namely whether one or more cases of a sudden, premature cardiac death have already occurred in the patient's family. The physician likewise enters the answer given by the patient into the system as relevant information. In step (c), the program selects that modality or those examination modalities that is/are relevant on the basis of the existing information and also selects corresponding, suitable examination or measurement protocols for each examination modality. As FIG. 1A shows, there is also the possibility in the exemplary embodiment of not implementing step (b), so that the system does not further analyze the informational content of the originally acquired anamnesis data, but merely undertakes the selection of the examination modalities and suitable protocols.

The method is configured dependent on the respective method mode, i.e. whether step (b) is implemented or not. When step (b) is not implemented, then three imaging examination modalities to be successively implemented are selected and displayed at a monitor of the data processing system. First, this is a conventional X-ray examination in order to investigate a possible anomaly of the shape of the heart. The X-ray examination is followed by an echocardiography in order, when no anomaly of the shape of the heart is found, to investigate a possible valve insufficiency. If such a finding is not present (as here), then a magnetic resonance examination is proposed as a third examination modality in order to investigate a possible dysplasia of the right ventricle.

According to this proposed sequence, thus, the conventional X-ray examination ensues first, from which no finding is identified in the illustrated example ("no" in the right column of FIG. 1A). No indication of a potential valve insufficiency ("no") is found, either, in the following echocardiography, for which reason the magnetic resonance examination is used as the next examination modality. This shall be discussed below.

A somewhat different method execution occurs when step (b) is implemented. In this case, the question about a sudden, premature cardiac death that may have occurred in the patient's family is answered "yes". The program evaluates the given information and proposes the immediate implementation of the magnetic resonance examination since the suspicion of a dysplasia of the right ventricle is established. Neither a conventional X-ray exam nor an echocardiography is implemented.

Different examinations with the magnetic resonance system are then implemented in step (d). As described, the data processing device communicates with the data processing and control device of the magnetic resonance apparatus. Relevant data and information, particularly the examination of measurement protocols that the data bank selected in the present case, are transmitted to the data processing device and/or control device at the side of the magnetic resonance apparatus. Information that relate to the following examination or that are relevant for the most recent diagnosis of suspected dysplasia can be previously output to the attending physician, for example at the picture screen of the data processing device. For example, the physician can be informed that the examination in such a case ensues in view of a potentially enlarged right ventricle or an enlarged discharge tract of the right ventricle as well as an aneurysm condition of the right ventricle and a fat infiltration of the right ventricular myocardium, since these symptoms are characteristic of a dysplasia. For example, guidelines of the "European Heart Association" can be displayed to the physician in the exemplary case or further information relating to the selected protocols, etc.

As a result of the transmission according to step (d), the relevant data are now present at the examination modality, i.e. at the magnetic resonance system here. They are made available to the attending physician or to the medical-technical radiology assistant. Among other things, this information also contains information as to positioning of the image plane, i.e. of the tomographic image plane, that is placed through the examination region. This can ensue, for example, by the radiology assistant being shown the position of the image plane on the basis of an image of such an examination region that was registered earlier and that has a marking entered therein, for example in the form of a line or the like.

The exposure (scan) ensues after all relevant parameters have been set. In the present example, whereby the exposure of the right ventricle ensues first in order to find whether this is enlarged. This is followed by the logging of this examination step as well as if warranted, the analysis in the system, i.e. the measurement of image segments needed for determining the size, the scope or another feature of a relevant organ or section of an organ.

Exposures are subsequently registered for evaluating the right ventricular discharge tract in order to be able to evaluate whether aneurysmic conditions exist. Here, as well, the radiology assistant is provided with corresponding positioning information, whether in the form of separate images or in the form of a video clip or the like. After the exposure has been made, the logging and if warranted, the measurement also ensue. Finally, exposures are made for detecting a fat infiltration in the right ventricular myocardium in order to be able to examine an incorporation of fat in this region. Here, as well, the radiology assistant is shown corresponding positioning information and other relevant information at the monitor at the apparatus, this information having been selected from the data bank.

After the exposure of all relevant images has ensued, the exposures are presented in step (e). At the same time, comparison images or comparison video clips that show a healthy or a diseased examination region can be allocated to the respective exposures, so that the physician, who now must analyze and evaluate the images, can make a comparison of the patient image to a definitively healthy or definitively pathological comparison image in a simple way. Any evaluation results that were acquired previously are also output, for instance calculated results relating to the size or length or the scope of an organ or a section of an organ, etc., corresponding comparison values of a healthy or of a diseased organ or section of an organ being compared thereto.

In the present case, first, the calculated ventricular volume of the patient, which was identified from the exposure of the right ventricle, is compared to the ventricular volume of a normal, healthy patient. Based thereon, the physician can now answer the question as to whether the ventricle is enlarged. His/her diagnosis is entered into the system. It should be noted that this presentation of the exposures as well as the entry of the data can ensue at the magnetic resonance system itself—the data, for example, are then transmitted to the data processing device where the program resides. After transmission of the image data to the data processing device, alternatively, there is also the possibility of undertaking all analyses thereat.

In addition to the ventricle volume, further, the diameter of the right ventricular discharge tract also is compared to the diameter of the left ventricular discharge tract. The two diameters can be identified on the basis of the exposures for evaluating the discharge tract. Conclusions can be drawn therefrom as to whether an aneurysmic condition is indicated. Finally, the exposure or exposures made for determining the existence of fat infiltration are presented, possibly together with a comparison image, in order to then determine whether a fat infiltration is indicated.

The physician enters his/her finding for every analysis step. The program employs this information in order to make a proposal therefrom relating to the further treatment of the patient. If all suspicions of a right ventricular dysplasia are confirmed in the present instance, then, for example, the program proposes that an intra-operative transmural biopsy be undertaken for confirming this diagnosis made by the physician.

In addition, the program can support the physician in the formulation of the findings, for example, by including pre-formulated findings texts that can be combined into an overall finding on the basis of the diagnosed results.

Although modifications and changes may be suggested by those skilled in the art, it is the intention of the inventor to embody within the patent warranted hereon all changes and modifications as reasonably and properly come within the scope of his contribution to the art.

The invention claimed is:

1. A method for processing medically relevant information for examining a patient, comprising the steps of:
    (a) storing a program, including a data bank containing stored data selected from the group consisting of symptom-based data and diagnosis-based data, in a data processor;
    (b) entering patient-specific information, selected from the group consisting of symptom-specific information and diagnosis-specific information, into said data processor;
    (c) executing said program in said data processor to select at least one examination modality for an examination of said patient dependent on said stored data and said patient-specific information and generating a protocol to operate said at least one examination modality, selected from the group consisting of examination protocols and measurement protocols, for conducting said examination; and
    (d) making output information relating to the selected modality available from said data processor and including said protocol in said output information.

2. A method as claimed in claim 1 wherein step (c) comprises selecting a plurality of examination modalities and designating a sequence for examining said patient respectively with said plurality of examination modalities.

3. A method as claimed in claim 1 wherein step (b) comprises, after entering said patient-specific information into said data processor, executing said program in said data processor to generate at least one question, and presenting said question to said patient and obtaining a reply from said patient, and entering said reply into said data processor to augment said patient-specific information used in step (c).

4. A method as claimed in claim 1 wherein said selected modality is an imaging modality having an image plane associated therewith, and wherein the step of generating said protocol comprises generating positioning information, selected from the group consisting of optical information and acoustic information, for said image plane.

5. A method as claimed in claim 4 wherein said positioning information is optical information, and wherein step (d) comprises displaying an examination region of said patient to be examined using said selected image modality, mixed with at least one marking, as said optical information, designating a position of said image plane in said examination region.

6. A method as claimed in claim 5 comprising displaying a previously registered image of said patient as said examination region.

7. A method as claimed in claim 1 comprising the additional step of examining said patient with said selected examination modality and thereby obtaining examination information, and entering said examination information into said data processor to augment said patient-specific information, and repeating step (c) to select a further examination modality for a further examination of said patient, and wherein step (d) comprising making output information relating to the selecting further modality available from said data processor.

8. A method as claimed in claim 1 wherein step (d) comprising making additional information selected from the group consisting of additional examination-relevant information and additional diagnosis-related information available in said output information.

9. A method as claimed in claim 1 comprising the additional step of examining said patient using said selected examination modality and thereby obtaining an examination image of an examination region of said patient, and displaying a comparison image of said examination region.

10. A method as claimed in claim 9 comprising displaying said examination image and said comparison image together in common at a monitor.

11. A method as claimed in claim 1 wherein step (d) comprises executing said program to select data from said stored data in said data bank, dependent on said patient-specific information, which more specifically describe a condition of said patient, and including said data in said output information.

12. A method as claimed in claim 1 comprising the additional steps of:
    establishing a communication link between said data processor and an examination device for performing said selected examination modality; and
    transmitting said output information to said examination device via said communication link.

13. A method as claimed in claim 12 comprising displaying said output information at a display at said examination device.

14. A method as claimed in claim 12 comprising controlling said examination device dependent on said output information.

15. A system for processing medically relevant information for examining a patient, comprising:
    a data processor in which storing a program, including a data bank containing stored data selected from the group consisting of symptom-based data and diagnosis-based data, is stored;
    said data processor allowing entry therein of patient-specific information, selected from the group consisting of symptom-specific information and diagnosis-specific information;
    said data processor executing said program to select at least one examination modality for an examination of said patient dependent on said stored data and said patient-specific information and generates a protocol to operate said at least one examination modality, selected from the group consisting of examination protocols and measurement protocols, for conducting said examination; and an output unit in communication with said data processor making output information relating to the selected modality available from said data processor, said output unit including said protocol in said output information.

16. A system as claimed in claim 15 wherein said data processor selects a plurality of examination modalities and designates a sequence for examining said patient respectively with said plurality of examination modalities.

17. A system as claimed in claim 15 wherein said data processor, after entry of said patient-specific information into said data processor, executes said program to generate at least one question, and makes said question available to said patient via said output device and allows entry of a reply from said patient into said data processor to augment said patient-specific information used to select said modality.

18. A system as claimed in claim 15 wherein said selected modality is an imaging modality having an image plane associated therewith, and wherein said data processor in generating said protocol generates positioning information, selected from the group consisting of optical information and acoustic information, for said image plane.

19. A system as claimed in claim 18 wherein said positioning information is optical information, and wherein said output unit displays an examination region of said patient to be examined using said selected image modality, mixed with at least one marking, as said optical information, designating a position of said image plane in said examination region.

20. A system as claimed in claim 19 comprising wherein said output unit displays a previously registered image of said patient as said examination region.

21. A system as claimed in claim 15 wherein said data processor after said patient with is examined said selected examination modality and to obtain examination information, allows entry of said examination information into said data processor to augment said patient-specific information, and selects a further examination modality for a further examination of said patient, and wherein said output unit makes output information relating to the selecting further modality available from said data processor.

22. A system as claimed in claim 15 wherein said output unit makes additional information selected from the group consisting of additional examination-relevant information and additional diagnosis-related information available in said output information.

23. A system as claimed in claim 15 wherein after examining said patient using said selected examination modality and thereby obtaining an examination image of an examination region of said patient, said output unit displays a comparison image of said examination region.

24. A system as claimed in claim 23 wherein said output unit displays said examination image and said comparison image together in common at a monitor.

25. A system as claimed in claim 15 wherein said data processor executes said program to select data from said stored data in said data bank, dependent on said patient-specific information, which more specifically describe a condition of said patient, and wherein said output unit includes said data in said output information.

26. A system as claimed in claim 15 further comprising:
a communication link between said output unit and an examination device for performing said selected examination modality; and
wherein said output unit transmits said output information to said examination device via said communication link.

27. A system as claimed in claim 26 comprising a display at said examination device for displaying said output information.

28. A system as claimed in claim 26 wherein said examination device is controlled dependent on said output information.

* * * * *